United States Patent
Pinna et al.

(10) Patent No.: US 7,612,048 B2
(45) Date of Patent: *Nov. 3, 2009

(54) QUICK WATER-DISSOLVING FILM CONTAINING COSMETIC, AROMATIC, PHARMACEUTICAL OR FOOD SUBSTANCES

(75) Inventors: Marco Pinna, Induno Olona (IT); Fausto Pinna, Lesmo (IT)

(73) Assignee: Biofarmitalia S.p.A., Milan (IT)

( * ) Notice: Subject to any disclaimer, the term of this patent is extended or adjusted under 35 U.S.C. 154(b) by 463 days.

This patent is subject to a terminal disclaimer.

(21) Appl. No.: 10/673,178

(22) Filed: Sep. 30, 2003

(65) Prior Publication Data

US 2004/0086539 A1    May 6, 2004

(30) Foreign Application Priority Data

Nov. 5, 2002    (IT) .......................... MI2002A2343

(51) Int. Cl.
*A01N 43/04*    (2006.01)

(52) U.S. Cl. .......................... 514/57; 514/60; 514/778; 514/781; 424/93.45

(58) Field of Classification Search .................. 514/60, 514/57, 778, 781; 424/93.45
See application file for complete search history.

(56) References Cited

U.S. PATENT DOCUMENTS

| | | | |
|---|---|---|---|
| 4,317,838 A | | 3/1982 | Cherukuri et al. |
| 4,345,032 A | * | 8/1982 | Hata ........................ 435/252.9 |
| 5,206,026 A | * | 4/1993 | Sharik ........................ 424/445 |
| 5,368,861 A | * | 11/1994 | Ushimaru et al. ........... 424/451 |
| 5,716,615 A | * | 2/1998 | Cavaliere Vesely et al. 424/93.4 |
| 6,419,903 B1 | * | 7/2002 | Xu et al. ........................ 424/49 |

FOREIGN PATENT DOCUMENTS

| | | |
|---|---|---|
| EP | 0 449 782 | 10/1991 |
| EP | 0 547 551 | 6/1993 |
| EP | 1 245 577 | 10/2002 |
| GB | 2 079 129 | 1/1982 |
| WO | WO 95/01735 | 1/1995 |
| WO | WO 02/102173 | 12/2002 |

OTHER PUBLICATIONS

The Random House College Dictionary, Revised Edition. Stein, J ed. 1980. Random House, Inc. p. 159.*

* cited by examiner

*Primary Examiner*—Leon B. Lankford
*Assistant Examiner*—Susan E. Fernandez
(74) *Attorney, Agent, or Firm*—Oblon, Spivak, McClelland, Maier & Neustadt, L.L.P.

(57) ABSTRACT

Film with high solubility in water, comprising a starch, a cellulose and a cosmetic, aromatic, pharmaceutical and/or food substance in a quantity exceeding 10% on the total film weight.

8 Claims, No Drawings

QUICK WATER-DISSOLVING FILM CONTAINING COSMETIC, AROMATIC, PHARMACEUTICAL OR FOOD SUBSTANCES

FIELD OF THE INVENTION

The present invention relates to a process and to formulations arranged to give a thin edible film easily dissolved in water, such that on inserting a small leaf into the mouth, it dissolves within a few seconds when in contact with the saliva.

Such a film is very useful as it can incorporate within its interior active ingredients of cosmetic, pharmaceutical, dietetic or food type, enabling them to be easily and immediately administered.

BACKGROUND OF THE INVENTION

According to the known art, the film thickness varies from a minimum of microns to a maximum of 70 microns. The film dissolving time clearly increases on increasing the thickness. The ideal, to achieve a dissolving time of a few seconds, is to maintain the thickness around 35÷45 microns. To be of practical applicability, the surface of a film usable for cosmetic, food or pharmaceutical purposes must have an area of about ⅝ $cm^2$ and a weight variable between 25 and 35 milligrams.

DISCUSSION OF THE KNOWN ART

The weight of the active ingredients present in known films is small compared with the total film weight, being on an average about 4-10% of that weight; beyond 10%, however, the film characteristics alter to make the film unsuitable for practical use: if an attempt is made to increase this percentage to 20%, the final film structure (fragility, softness, etc.) is considerably influenced to the extent that the advantages claimed in said patents are completely lost.

It could be objected that to obtain a greater dose of active principle it would be sufficient to double, triple or quadruple the administered dose, however this would be disadvantageous and hardly practical compared with a single administration.

Another limit noted in the preceding inventions is the fact that the initial mixture, prepared at ambient temperature, often contains considerable quantities of ethanol, the active principles being dispersed in the said mixture. For certain types of active ingredients, this operation is deleterious, an example being food bacteria such as lactic acid, probiotic, prebiotic and symbiotic cultures which, when fed into such a solution, would be immediately killed. This applies in particular to all groups of lactic bacteria (*lactobacillus acidophilus, lactobacillus gasseri, lactobacillus johsonii, lactobacillus crispatus, lactobacillus amylovorus, lactobacillus gallinarum; lactobacillus casei* subsp. casei, *lactobacillus paracasei* subsp. paracasei, *lactobacillus rhamnosus; lactobacillus reuteri, lactobacillus plantarum, lactobacillus salivarius, pediococcus acidilactici, lactobacillus delbrueckii* subsp. bulgaricus, *Streptococcus thermophilus*, etc.), all the bifidobacteria (*bifidobacterium longum*, bifidum, brevibacterium, infantis, adolescentis, lactis, etc.), and other non-lactic bacteria and non-bifidobacteria microorganisms (*Enterococcus faecium, bacillus subtilis, bacillus coagulans (Lactobacillus sporogenes), saccharomyces cerevisiae*, etc.). These bacteria are also sensitive to pressure and temperature, so that the classical supports, such as tablets, given the considerable use of pressure necessary for their formation, would result in destruction of the bacteria. The ability therefore to maintain them alive in a large number in the finished product would be of considerable interest in all dairy milk processes, for which leaves could be provided which are ready and sized for easy and immediate use.

SUMMARY OF THE INVENTION

The present invention has the object to provide an edible film which obviates said drawbacks by containing high percentages (greater than those obtainable by the teachings of the known art) of therapeutic, food or cosmetic active principles, or disinfectant-sensitive bacteria, the film having good dimensional stability such as to be able to be produced in a very small thickness, between 10 and 70 microns, suitable for punching or cutting into small formats, and which can be easily inserted into the mouth into a position above or below the tongue, and is rapidly dissolvable in contact with the mouth saliva.

This film is a quick water-dissolving film containing cosmetic, aromatic, pharmaceutical and/or food substances, and consisting of:

at least one starch of low molecular weight and high amylopectin content at least one cellulose compatible with said starch, and at least one cosmetic, aromatic, pharmaceutical and/or food substance, said substance being present in a quantity exceeding 10% on the total film weight.

Preferably, said food substance is chosen from the group comprising probiotic, prebiotic and symbiotic food bacteria; more preferably, said food bacteria are chosen from the group consisting of lactic bacteria, bifidobacteria, and other microorganisms (non-lactic bacteria and non-bifidobacteria), and said cellulose consists of hydroxypropylmethylcellulose and/or hydroxyethylcellulose.

The process for producing the film of the invention comprises the steps of feeding water, ethanol and at least one starch into a mixer, stirring at a temperature between 80° C. and 100° C. until the starch has dissolved and caramelized, adding at least one cellulose compatible with the starch and stirring until a homogeneous mass substantially free of ethanol is obtained, then cooling to a temperature between 25° C. and 35° C., adding said substances and stirring until a homogeneous mass is obtained, which is spread with a doctor blade assembly onto the surface of a support web, heating in a through forced-air oven to a temperature between 30° C. and 40° C., cooling to ambient temperature, removing the film from the support and die-cutting it to the required size.

To obtain the aforedescribed product, numerous tests have shown that at least one of the following elements must be used:

a) at least one low molecular weight starch of high amylopectin content. The starch can be selected from those obtained from maize, wheat, potato, rice, soya, tapioca, etc. This starch must be present between a minimum of 20% and a maximum of 80% by weight on the final film composition.

b) at least one cellulose compatible with said starch, preferably chosen from the following substances: hydroxypropylcellulose, hydroxypropylmethylcellulose, hydroxyethylcellulose, carboxymethylcellulose. These polymers and celluloses must be present in the finished product (film) from a minimum of 15% to a maximum of 70% by weight.

Other ingredients the presence of which is preferred in producing the film are polysorbate 80, sorbitol, glycerol mono oleate, carrageenan, soya lecithin, colorants and methylsalicylate. Polyvinylalcohol, polyvinylpyrrolidone, polyethylene glycol and xanthan gum can also be present.

The procedure followed to bind the starch and cellulose in stable form is to dilute the starch and cellulose in ethanol and water in a jacketed mixer then, while stirring, bringing them to a temperature of 80-90° C. and maintaining them under stirring for at least 30 minutes to substantially eliminate the ethanol. Again while stirring, the mixture is brought again to a temperature around 30÷35° C. until a viscosity of 3÷8000 mPas is obtained. The product obtained in this manner is able to retain considerable quantities of active substances, up to 30% by weight of its own weight: after evaporating all the residual water, active substance percentages between 10% and 50% by weight on the finished product are achieved. Moreover, once the mixture has cooled to 30÷35° C. and having lost its ethanol load, alcohol-sensitive substances such as lactic ferments, microorganisms or bacteria can be added to the mixture. This mixture is maintained under stirring and passed through a doctor blade assembly which does not compress the product and is able to distribute the product in the form of a thin film onto an antiadherent support which travels through a ventilated tunnel heated to 30÷35° C. to form the final film. This film is then separated from the anti-adherent support by known methods and die-cut into the required shape and size, then inserted into the final package.

EXAMPLE 1

The Components Of Two Separate Phases Known As "Phase A" And "Phase B" Are Used.

Phase A comprises:

| | |
|---|---|
| $H_2O$ | 150 g |
| ethanol | 150 g |
| hydroxypropylmethylcellulose | 50 g |
| oxidized starch | 20 g |
| polyvinyl alcohol | 15 g |
| polyethylene glycol | 4 g |
| glycerin | 2 g |
| sorbitol | 2 g |
| colorant | |

Phase B comprises a mixture of aromatic essential oils (30 g) and aspartame (1 g).

The components of Phase A are fed into a jacketed closed mixer in the following succession: water, ethanol and oxidized starch are firstly fed and stirred at medium speed and the temperature brought to 80° C., stirring being continued until the starch has dissolved and caramelized, to obtain a homogeneous solution.

While stirring, the temperature is brought to 90° C. and stirring maintained (at about 60 r.p.m.) for 30 minutes, then hydroxypropylmethylcellulose, polyethylene glycol and colorant are added and stirring continued until the solution is homogeneous.

It is cooled to 35° C., glycerol and sorbitol are added and stirring is maintained for 15 minutes. The temperature is brought to 30° C. and Phase B, previously mixed at ambient temperature, is slowly added. Stirring is maintained for 15 minutes. Using a peristaltic pump, the mixed product is withdrawn and made to flow onto a doctor blade assembly heated to 30° C., through which there passes a siliconized polyester web on which the product is deposited as a film to a thickness of 70 microns. The product (deposited as a film on polyester) is passed through a forced-air oven heated to 35° C. On leaving the oven the film is detached from the polyester support, and die-cut with a roller die into 2.3×3.3 cm rectangles, and the rectangles obtained are inserted into a container which is sealed.

Each rectangle obtained has a thickness of 35 microns, the time for its dissolving in the mouth being 6 seconds. The quantity of essential oils present is measured by HPLC, the result being the following:

| | |
|---|---|
| weight of rectangle (2.3 × 3.3 cm) | 25 mg |
| quantity of aromatic essential oils present | 7 mg |

EXAMPLE 2

As in Example 1 the components of two different compositions known as "Phase A" and "Phase B" are used.

The components of Phase A are:

| | |
|---|---|
| $H_2O$ | 150 g |
| ethanol | 150 g |
| hydroxyethylcellulose | 50 g |
| polyvinyl pyrrolidone | 25 g |
| hydroxypropylmethylcellulose | 35 g |
| oxidized starch | 20 g |
| xanthan gum | 10 g |
| polysorbate 80 | 2 g |
| methyl salicylate | 2 g |
| sorbitol | 2 g |
| colorant | |

The components of Phase B are:

| | |
|---|---|
| mixture of aromatic essential oils | 50 g |
| aspartame | 1 g |

The components of Phase A, i.e. firstly water, ethanol and oxidized starch, are fed into a jacketed closed mixer, then stirred at medium speed and the temperature brought to 80° C., stirring then being continued until a homogeneous solution is obtained.

While stirring, the temperature is brought to 90° C. and stirring maintained for 30 minutes, then hydroxyethylcellulose, polyvinyl pyrrolidone, hydroxypropylmethylcellulose, xanthan gum and colorant are added and stirring continued until the solution is homogeneous.

It is cooled to 35° C., polysorbate 80, methylsalicylate and sorbitol are added and stirring is maintained for 15 minutes.

The temperature is brought to 30° C. and Phase B, previously mixed at ambient temperature, is slowly added. Stirring is maintained for 15 minutes. Using a peristaltic pump, the mixed product is withdrawn and made to flow onto a doctor blade assembly heated to 30° C., through which there passes a siliconized polyester support web on which the product is deposited as a film to a thickness of 70 microns. The product deposited as a film on the polyester web is passed through a forced-air oven heated to 35° C. On leaving the oven the film is detached from the polyester support, and die-cut with a roller die into 2.3×3.3 cm rectangles. The rectangles obtained are packaged in a sealed container.

The rectangles obtained have a thickness of 40 microns, the time for their dissolving in the mouth being 6 seconds. The quantity of essential oils present is measured by HPLC, the result being the following:

| | |
|---|---|
| weight of rectangle (2.3 × 3.3 cm) | 30.5 mg |
| quantity of oils present | 7.6 mg |

EXAMPLE 3

As in the preceding examples, components of Phase A and components of Phase B are used.

The components of Phase A are:

| | |
|---|---|
| H₂O | 150 g |
| ethanol | 150 g |
| hydroxypropylmethylcellulose | 50 g |
| oxidized starch | 40 g |
| carrageenan | 10 g |
| polyethylene glycol 400 med | 4 g |
| soya lecithin | 10 g |
| methyl salicylate | 1 g |
| colorant | |

The components of Phase B are:

| | |
|---|---|
| mixture of aromatic essential oils | 40 g |
| aspartame | 1 g |

Phase A is fed into a jacketed closed mixer in the following manner: water, ethanol and oxidized starch, are firstly fed in, then stirred at medium speed and the temperature brought to 80° C., stirring then being continued until dissolution takes place to obtain a homogeneous solution.

While stirring, the temperature is brought to 90° C. and stirring maintained for 30 minutes, then hydroxypropylmethylcellulose, carrageenan and colorant are added and stirring continued until the solution is homogeneous.

It is cooled to 35° C., polyethylene glycol 400 med, soya lecithin and methylsalicylate are added and stirring is maintained for 15 minutes. The temperature is brought to 30° C. and Phase B, previously mixed at ambient temperature, is slowly added, and stirring is maintained for 15 minutes. Using a peristaltic pump, the mixed product is withdrawn and made to flow onto a doctor blade assembly heated to 30° C., through which there passes a siliconized polyester support web on which the product is deposited as a film to a thickness of 70 microns. The product deposited as a film on the polyester web is passed through a forced-air oven heated to 35° C. On leaving the oven the film is detached from the polyester support, and die-cut with a roller die into 2.3×3.3 cm rectangles. The rectangles obtained are packaged in a hermetically sealed container.

Each rectangle obtained has a thickness of 33 microns, the time for its dissolving in the mouth being 5 seconds. The quantity of essential oils present is measured by HPLC, the result being the following:

| | |
|---|---|
| weight of rectangle (2.3 × 3.3 cm) | 26 mg |
| quantity of oils present | 6.5 mg |

EXAMPLE 4

Again a Phase A is used, comprising:

| | |
|---|---|
| H₂O | 150 g |
| ethanol | 150 g |
| oxidized starch | 60 g |
| hydroxypropylmethylcellulose | 50 g |
| carrageenan | 10 g |
| polyethylene glycol | 4 g |
| glycerol | 2 g |
| sorbitol | 2 g |
| colorant | | together with a Phase B comprising food bacteria consisting of 100 g of lyophilized lactic ferments (*lactobacillus paracasei*).

Phase A is fed into a jacketed closed mixer in the following manner: water, ethanol and oxidized starch, are firstly fed in, then stirred at medium speed and the temperature brought to 80° C., stirring then being continued until the starch has dissolved to obtain a homogeneous solution.

While stirring, the temperature is brought to 90° C. and stirring maintained for 30 minutes, then hydroxypropylmethylcellulose, carrageenan and colorant are added and stirring continued until the solution is homogeneous. It is cooled to 35° C., polyethylene glycol 400 med, glycerol and sorbitol are added and stirring is maintained for 15 minutes. The temperature is brought to 30° C. and the probiotics, previously mixed at ambient temperature, are slowly added. Stirring is maintained for 15 minutes after which, using a peristaltic pump, the mixed product is withdrawn and made to flow onto a doctor blade assembly heated to 30° C., through which there passes a siliconized polyester support web on which the product is deposited as a film to a thickness of 70 microns. The product deposited as a film on the polyester web is passed through a forced-air oven heated to 35° C. On leaving the oven the film is detached from the polyester support, and die-cut with a roller die into 2.3×3.3 cm rectangles. The rectangles obtained in this manner from the film are packaged in a sealed container.

Each rectangle obtained has a thickness of 45 microns, the time for its dissolving in the mouth being 7 seconds. The quantities of microorganisms present were measured by a microscope, the result being the following:

| | |
|---|---|
| weight of rectangle (2.3 × 3.3 cm) | 34 mg |
| quantity of *lactobacillus paracasei* | about 1,500,000,000 units. |

The invention claimed is:

1. An edible film, comprising:
    at least one oxidized starch, the at least one oxidized starch being present in an amount of from 20 to 80 % by weight relative to the total weight of the film;
    at least one cellulose compound selected from the group consisting of hydroxypropylcellulose, hydroxypropylmethylcellulose, hydroxyethylcellulose and carboxymethylcellulose, the at least one cellulose compound being present in an amount of from 15 to 70 % by weight relative to the total weight of the film; and
    at least one active substance selected from the group consisting of a cosmetic substance, an aromatic substance, a pharmaceutical substance and a food substance, the at least one active substance being present in an amount of from 10 to 50 % by weight relative to the total weight of the film;
    wherein:
    the at least one oxidized starch and the at least one cellulose compound are chemically bonded to one another; and
    the film is composed so that the film will dissolve within 10 seconds of contact with saliva.

2. The film as claimed in claim 1, wherein the at least one active substance is selected from the group consisting of probiotic food bacteria, prebiotic food bacteria and symbiotic food bacteria.

3. The film as claimed in claim 1, wherein the at least one active substance is selected from the group consisting of lactic bacteria, bifidobacteria, non-lactic bacteria and non-bifidobacteria microorganisms.

4. The film as claimed in claim 1, wherein the at least one cellulose compound is at least one of hydroxypropylmethylcellulose and hydroxyethylcellulose.

5. The film as claimed in claim 2, wherein the at least one cellulose compound is at least one of hydroxypropylmethylcellulose and hydroxyethylcellulose.

6. The film as claimed in claim 3, wherein the at least one cellulose compound is at least one of hydroxypropylmethylcellulose and hydroxyethylcellulose.

7. The film as claimed in claim 1, wherein the film is composed so that the film will dissolve within 7 seconds of contact with saliva.

8. The film as claimed in claim 1, wherein the film is composed so that the film will dissolve within a few seconds of contact with saliva.

* * * * *